US008008230B2

(12) United States Patent
Garnier

(10) Patent No.: US 8,008,230 B2
(45) Date of Patent: Aug. 30, 2011

(54) SYNERGISTIC ANTIFUNGAL DDAC COMPOSITIONS

(75) Inventor: Alain Joseph Jean Florimond Garnier, Turnhout (BE)

(73) Assignee: Janssen Pharmaceutica N.V. (BE)

( * ) Notice: Subject to any disclaimer, the term of this patent is extended or adjusted under 35 U.S.C. 154(b) by 1010 days.

(21) Appl. No.: 10/588,321

(22) PCT Filed: Feb. 3, 2005

(86) PCT No.: PCT/EP2005/050463
§ 371 (c)(1),
(2), (4) Date: Aug. 3, 2006

(87) PCT Pub. No.: WO2005/074684
PCT Pub. Date: Aug. 18, 2005

(65) Prior Publication Data
US 2007/0142410 A1    Jun. 21, 2007

(30) Foreign Application Priority Data
Feb. 4, 2004    (EP) .................................... 04100400

(51) Int. Cl.
A01N 43/00    (2006.01)
(52) U.S. Cl. .................... 504/139; 504/101; 504/129
(58) Field of Classification Search ................ 514/357; 504/101, 129, 139
See application file for complete search history.

(56) References Cited

U.S. PATENT DOCUMENTS

| 4,061,750 | A |   | 12/1977 | Lada et al. | |
|---|---|---|---|---|---|
| 5,013,748 | A |   | 5/1991 | Radtke et al. | |
| 5,547,990 | A | * | 8/1996 | Hall et al. ..................... | 514/563 |
| 6,207,695 | B1 | * | 3/2001 | Nelson et al. ................. | 514/399 |
| 6,423,732 | B1 |   | 7/2002 | Rustenburg et al. | |
| 6,797,301 | B1 |   | 9/2004 | Duvert et al. | |
| 2003/0199490 | A1 | * | 10/2003 | Antoni-Zimmermann et al. ............................ | 514/184 |
| 2004/0044060 | A1 |   | 3/2004 | Muller et al. | |
| 2005/0118280 | A1 |   | 6/2005 | Leach et al. | |
| 2008/0234336 | A1 |   | 9/2008 | Garnier et al. | |
| 2009/0061021 | A1 |   | 3/2009 | Thys et al. | |
| 2009/0275584 | A1 |   | 11/2009 | Bylemans et al. | |

FOREIGN PATENT DOCUMENTS

| DE | 3242646 A | 6/1983 |
|---|---|---|
| DE | 19834629 A | 12/1998 |
| EP | 0328466 A | 8/1989 |
| EP | 0554833 A | 8/1993 |
| EP | 0336489 B1 | 8/1995 |
| EP | 0741971 A2 | 11/1996 |
| EP | 1563731 A | 8/2005 |
| GB | 2110934 A | 6/1983 |
| GB | 2354771 A | 4/2001 |
| JP | 2000-103709 A | 4/2000 |
| WO | WO 92/19286 A | 11/1992 |
| WO | WO 97/40682 A1 | 11/1997 |
| WO | WO 98/56366 A | 12/1998 |
| WO | WO 99/12411 A2 | 3/1999 |
| WO | WO 99/12422 A1 | 3/1999 |
| WO | WO 02/054869 A1 | 7/2002 |
| WO | WO 03/011030 A1 | 2/2003 |
| WO | WO 2006/021556 A | 3/2006 |

OTHER PUBLICATIONS

Derwent Publications Ltd., Section Ch, Week 198637, XP002294179, Aug. 18, 1986 (abstract).
T. Kuramoto et al, "DF-125, A new experimental fungicide for the control of Satsuma mandarin", XP002323612, vol. 60, No. 10, 1976, pp. 809-812.
P. Sholberg et al., "Evaluation of Fungicides for Brown Rot Control", XP002323613, (1988) (abstract).
Search report for International Appl. No. PCT/EP/050463.
International Search Report and Written Opinion of the International Searching Authority relating to International Patent Application No. PCT/EP2006/066859, which corresponds to U.S. Appl. No.12/067,558, Date of Mailing: Jan. 22, 2007.
International Search Report and Written Opinion of the International Searching Authority relating to International Patent Application No. PCT/EP2007/052081, which corresponds to U.S. Appl. No. 12/281,874, Date of Mailing: Apr. 23, 2007.
International Search Report and Written Opinion of the International Searching Authority relating to International Patent Application No. PCT/EP2007/054238, which corresponds to U.S. Appl. No. 12/299,130, Date of Mailing: Aug. 31, 2007.
Richter, D.L., "Synergism—a patent view.", Pestic. Sci. 1987, pp. 309-315, vol. 19(4).
Kull et al., "Mixtures of Quaternary Ammonium Compounds and Long-chain Fatty Acids as Antifungal Agents.", Applied Microbiology, 1961, pp. 538-541, vol. 9(6).
Steinberg, D.C., "Measuring synergy", Cosmetics & Toiletries, Nov. 2000, pp. 59-62, vol. 115(11).
Zwart Voorspuij, A.J., and C.A.G. Nass, "Some aspects of the notions additivity, synergism and antagonism in the simultaneous activity of two antibacterial agents in vitro" Arch. Intel. Pharmacodyn Ther., Jan. 1, 1957, pp. 211-228, vol. 109(1-2).
Derwent Publications Ltd., Section CH, Week 199517; AN 1995-131302, XP002383453.
Database CA, Chemical Abstracts Service, STN Database accession No. 2001:578597, Elsemore, Richard, et al., "Bactericide combinations in detergents" abstract; XP002419019, Date 1999.

* cited by examiner

Primary Examiner — Rebecca Prouty
Assistant Examiner — Danielle Sullivan
(74) Attorney, Agent, or Firm — Jeremy K. McKown

(57) ABSTRACT

The present invention relates to synergistic antifungal compositions comprising didecyl ammonium chloride (DDAC) and a post-harvest antifungal agent selected from the group consisting of imazalil, boscalid, fenhexamid, pyrimethanil, thiophanate-methyl, triflumizole, azoxystrobin, dimoxystrobin, picoxystrobin, and pyraclostrobin for protecting plants, fruit or seeds against phytopathogenic fungi.

4 Claims, No Drawings

SYNERGISTIC ANTIFUNGAL DDAC COMPOSITIONS

CROSS REFERENCE TO RELATED APPLICATIONS

This application is the national stage of Application No. PCT/EP2005/050463, filed Feb. 3, 2005, which application claims priority from European Patent Appl. No. 04100400.3, filed Feb. 4, 2004.

The present invention relates to synergistic antifungal compositions comprising didecyl ammonium chloride (DDAC) and a post-harvest antifungal agent selected from the group consisting of imazalil, boscalid, fenhexamid, pyrimethanil, thiophanate-methyl, triflumizole, azoxystrobin, dimoxystrobin, picoxystrobin, and pyraclostrobin for protecting plants, fruit or seeds against phytopathogenic fungi.

Fungicidal combinations comprising the post-harvest antifungal agents imazalil, pyrimethanil or thiabendazole have been disclosed in, for example, WO-99/12422 which describes synergistic compositions of imazalil and epoxiconazole and WO-03/011030 which describes fungicidal compositions comprising pyrimethanil and imazalil. WO-98/56366 discloses compositions for use as an antimicrobial agent comprising a quaternary ammonium compound and a guanidinium component.

It has now been found that, within certain broad limits of composition (i.e. in certain respective proportions or amounts of the active ingredients) easily determinable by those skilled in the art, the combination of DDAC (hereinafter referred to as component I) and a post-harvest antifungal agent selected from the group consisting of imazalil, boscalid, fenhexamid, pyrimethanil, thiophanate-methyl, triflumizole, azoxystrobin, dimoxystrobin, picoxystrobin, and pyraclostrobin (hereinafter referred to as a component II), is able to provide a synergistic effect on the control of phytopathogenic fungi, i.e. a synergistic controlling or protecting effect against fungal growth on plants, fruit or seeds.

DDAC, component (I) is the generic name for didecyl dimethyl ammonium chloride which may be represented by the formula

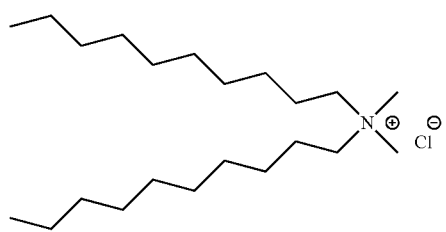

(I)

DDAC has bactericidal properties and is used in a great variety of application areas: as active ingredient in disinfectants, sanitizers, and cleaners for use in hospitals, homes, diary, farm, and industrial areas; as a water treatment microbicide for cooling towers and secondary oil recovery; as a microbicide for the protection of textile materials against permanent staining by the attack of mould-producing fungi and as active ingredient in solutions for the temporary protection of freshly sawn timber against the growth of wood discolouring fungi.

The post-harvest fungicidal components (II) are:

Imazalil, component (II-a), is a systemic fungicide with protective and curative action and is used to control a wide range of fungi on fruit, vegetables, and ornamentals, including powdery mildew on cucumber and black spot on roses. Imazalil is also used as a seed dressing and for post harvest treatment of citrus, banana, and other fruit to control storage decay. It is the generic name of the compound 1-[2-(2,4-dichlorophenyl)-2-(2-propenyloxy)ethyl)]-1H-imidazole, which compound may be represented by the formula

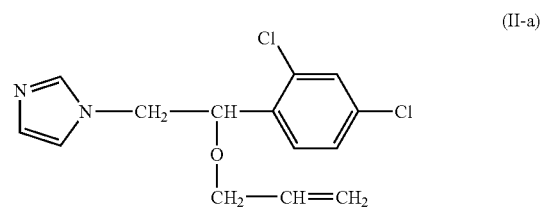

(II-a)

Boscalid, component (II-b), is a foliar fungicide used to control powdery mildew, *Alternaria, Botrytis, Sclerotinia*, and *Monilia* on a range of fruit and vegetables. It is the generic name for 2-chloro-N-(4'-chlorobiphenyl-2-yl)-nicotinamide which may be represented by the formula

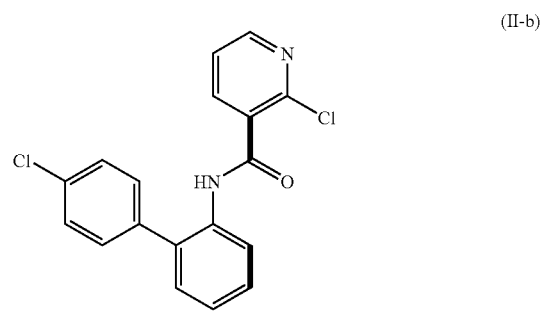

(II-b)

Fenhexamid, component (II-c), is a foliar fungicide used to control *Botrytis cinerea, Monilia* and related pathogens on grapes, berries, stone fruit, citrus, vegetables and ornamentals. It is the generic name for 2',3'-dichloro-4'-hydroxy-1-methylcyclohexanecarboxanilide which may be represented by the formula

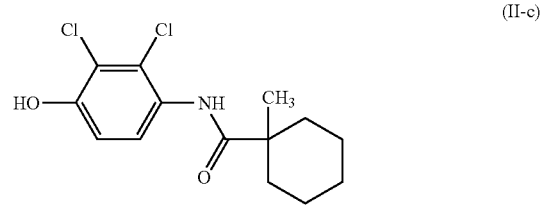

(II-c)

Pyrimethanil, component (II-d), is a fungicide with protective and curative action and is used to control grey mould on vines, fruit, vegetables and ornamentals. Said component (II-b) is the generic name for 4,6-dimethyl-N-phenyl-2-pyrimidinamine, which may be represented by the formula

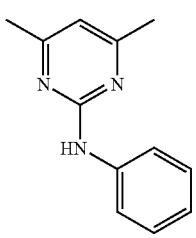

(II-d)

Thiophanate-methyl, component (II-e), is a systemic fungicide with protective and curative action and is used against a wide range of fungal pathogens in post-harvest treatment and seed-treatment. It is the generic name for 4,4'-(o-phenylene)bis(3-thioallophanate) which may be represented by the formula

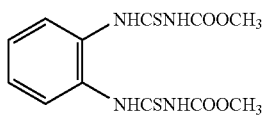

(II-e)

Triflumizole, component (II-f), is the generic name for (E)-4-chloro-α,α,α-trifluoro-N-(1-imidazol-1-yl-2-propoxyethylidene)-o-toluidine, which may be represented by the formula

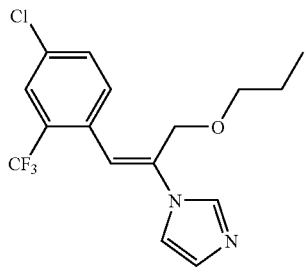

(II-f)

Triflumizole is a protectant fungicide to be used as a soil drench, foliar spray or through chemigation for control of diseases on ornamentals grown in enclosed commercial structures such as greenhouses, shade houses and interior landscapes.

Azoxystrobin, component (II-g), is a fungicide with protective, curative, eradicant, translaminar and systemic properties for disease control in cereals, vegetables and fruit. It is the generic name for methyl(E)-2-[2-[6-(2-cyano-phenoxy)pyrimidin-4-yloxy]phenyl]-3-methoxyacrylate which may be represented by the formula

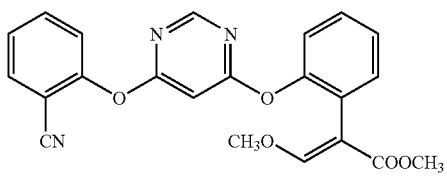

(II-g)

Dimoxystrobin, component (II-h), is a fungicide with protective, curative, and translaminar properties for disease control in cereals, vegetables and fruit. It is the generic name for (E)-2-(methoxyimino)-N-methyl-2-[α-(2,5-xylyloxy)-o-tolyl]acetamide which may be represented by the formula

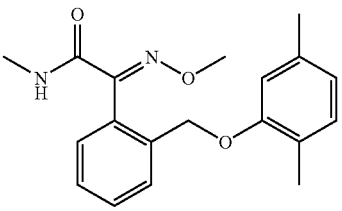

(II-h)

Picoxystrobin, component (II-i), is a fungicide with protective and curative properties for disease control in cereals, vegetables and fruit. It is the generic name for methyl(E)-3-methoxy-2-[2-(6-trifluoromethyl-2-pyridyloxymethyl)phenyl]acrylate which may be represented by the formula

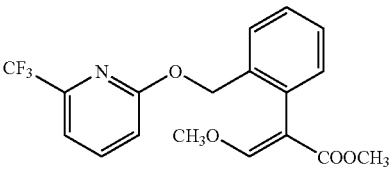

(II-i)

Pyraclostrobin, component (II-j), is a fungicide with protectant, curative, and translaminar properties for disease control in cereals, vegetables and fruit. It is the generic name for methyl N-(2-[1-(4-chlorophenyl)-1H-pyrazol-3-yloxymethyl]phenyl](N-methoxy)carbamate which may be represented by the formula

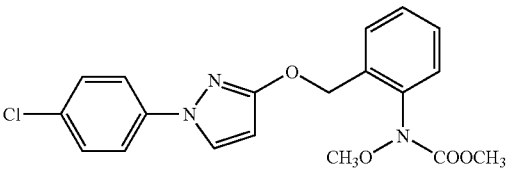

(II-j)

The post-harvest antifungal agents imazalil (II-a), boscalid (II-b), fenhexamid (II-c), pyrimethanil (II-d), thiophanate-methyl (II-e), triflumizole (II-f), azoxystrobin (II-g), dimoxystrobin (II-h), picoxystrobin (II-i), and pyraclostrobin (II-j) may be present in their free base form or in the form of an acid addition salt, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Particular salt forms of imazalil (II-a) are the sulfate, phosphate, acetate, nitrate or phosphite salts.

A particular salt form of pyrimethanil (II-d) is pyrimethanil oleate. Other salts of pyrimethanil such as the malonate, phthalate and the like have been described in WO-97/40682 on page 3 as compounds (2) to (13).

The components (I) and (II) for use in the compositions according to the present invention should preferably be present in a substantially pure form, i.e. free from chemical impurities (such as co-products or residual solvents) resulting from their manufacturing and/or handling processes in view to safely control the phytopathogenic fungi management programs for which they are intended. The term "substantially pure" as used hereinbefore means a purity (either chemical or optical), as determined by methods conventional in the art such as high performance liquid chromatography or optical methods, of at least about 96%, preferably at least 98% and more preferably at least 99%.

Imazalil (II-a) has one asymmetric carbon atom and can therefore be used in the embodied compositions in the form of a mixture of both enantiomers, in particular a racemic mixture, or in the form of a substantially pure (R)- or (S)-enantiomer. The term "substantially pure" as used hereinbefore means a purity (either chemical or optical), as determined by methods conventional in the art such as high performance liquid chromatography or optical methods, of at least about 96%, preferably at least 98% and more preferably at least 99%.

The compositions of the present invention are active against a broad range of phytophatogenic fungi. As examples of such fungi there may be named Ascomycetes (e.g. *Venturia, Podosphaera, Erysiphe, Monilinia, Uncinula, Aureobasidium, Sclerophoma*); Basidiomycetes (e.g. *Hemileia, Rhizoctonia, Puccinia, Coniophora, Serpula, Poria, Uromyces, Gloeophyllum, Lentinus, Coriolus, Irpex*); Fungi imperfecti (e.g. *Botrytis, Helminthosporium, Rhynchosporium, Fusarium, Septoria, Cercospora, Alternaia, Pyricularia, Penicillium, Geotrichum*).

The relative proportions of component (I) and one of the components (II) in the embodied compositions are those proportions which result in unexpected synergistic efficacy against fungi, especially against plant, fruit and seed pathogens, when compared to a composition including, as an active ingredient, either component (I) alone or one of the components (II) alone. As will readily be understood by those skilled in the art, the said synergistic efficacy may be obtained within various proportions of components (I) and (II) in the composition, depending on the kind of fungi towards which efficacy is measured and the substrate to be treated. Based on the teachings of the present application, determination of the synergistic or possibly (for some proportions of components (I) and (II) applied to specific fungi) non-synergistic efficacy of such compositions is well within the routine work of those skilled in the art. As a general rule, however, it may be said that for most phytopathogenic fungi the suitable proportions by weight of the amount of component (I) to component (II) in the active composition should lie in the range from 1:100 to 10:1, more preferably from 1:50 to 2:1.

The quantity of each of the active ingredients in the compositions according to the present invention will be so that a synergistic fungicidal effect is obtained. In particular it is contemplated that the compositions of the present invention comprise component (I) in a range from 10 to 1.000 mg/l. The component (II) is present in an amount ranging from 10 to 1.000 mg/l depending upon the specific activity of the selected component (II). For example component (II-a), i.e. imazalil, is present in a range from 10 to 1.000 mg/l, more preferably 500 mg/l.

The compositions according to the present invention comprise as component (I) DDAC and as component (II) a postharvest antifungal agent selected from the group consisting of imazalil (II-a), boscalid (II-b), fenhexamid (II-c), pyrimethanil (II-d), thiophanate-methyl (II-e), triflumizole (II-f), azoxystrobin (II-g), dimoxystrobin (II-h), picoxystrobin (II-i), and pyraclostrobin (II-j), in respective proportions such as to provide a synergistic antifungal effect, and one or more acceptable carriers.

These carriers are any material or substance with which the composition of components (I) and (II) is formulated in order to facilitate its application/dissemination to the locus to be treated, for instance by dissolving, dispersing, or diffusing the said composition, and/or to facilitate its storage, transport or handling without impairing its antifungal effectiveness. Said acceptable carriers may be a solid or a liquid or a gas which has been compressed to form a liquid, i.e. the compositions of this invention can suitably be used as concentrates, emulsions, emulsifiable concentrates, oil miscible suspension concentrates, oil-miscible liquid, soluble concentrates, solutions, granulates, dusts, sprays, aerosols, pellets, or powders.

In many instances the fungicidal compositions to be used directly can be obtained from concentrates, such as e.g. emulsifiable concentrates, suspension concentrates, or soluble concentrates, upon dilution with aqueous or organic media, such concentrates being intended to be covered by the term composition as used in the definitions of the present invention. Such concentrates can be diluted to a ready to use mixture in a spray tank shortly before use. Preferably the compositions of the invention should contain from about 0.01 to 95% by weight of the combination of components (I) and (II). More preferably this range is from 0.1 to 90% by weight. Most preferably this range is from 1 to 80% by weight, depending on the type of formulation to be selected for specific application purposes, as further explained in details hereinafter.

An emulsifiable concentrate is a liquid, homogeneous formulation of the components (I) and (II) to be applied as an emulsion after dilution in water. A suspension concentrate is a stable suspension of the active ingredients in a fluid intended for dilution with water before use. A soluble concentrate is a liquid, homogeneous formulation to be applied as a true solution of the active ingredients after dilution in water.

The fungicidal compositions of the present invention can also be formulated as waxes for use as a cover or coating of e.g. fruit, in particular citrus fruit.

The fungicidal compositions according to the present invention possess advantageous curative, preventive and anti-sporulant fungicidal activity to protect plants, fruit and seeds. The present mixtures can be used to protect plants or parts of plants, e.g. fruit, blossoms, flowers, foliage, stems, roots, cuttings, tubers of plants or culture plants infected, harmed or destroyed by micro-organisms, whereby later-growing parts of plants are protected against such micro-organisms.

As examples of the wide variety of culture plants in which the combinations of components (I) and (II) according to the present invention can be used, there may be named for example cereals, e.g. wheat, barley, rye, oats, rice, sorghum and the like; beets, e.g. sugar beet and fodder beet; pome and stone fruit and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruit, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugarcane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

A particular mode of administering an antifungal composition of the present invention, is the administration to the aboveground parts of plants, in particular to the leaves thereof (leaf-application). The number of applications and the administered doses are chosen in accordance with the biological and climatic conditions of life of the causative agent. The antifungal compositions though, can also be applied to the soil and get into the plants through the root system (systemic activity), in case the locus of the plants is sprayed with a liquid composition or if the components are added to the soil in a solid formulation e.g. in the form of a granulate (soil application).

The antifungal compositions of the present invention are particularly useful in post-harvest treatment of fruit, especially citrus fruit. In the latter instance, the fruit will be sprayed with or dipped or drenched into a liquid formulation or the fruit may be coated with a waxy composition. The latter waxy composition conveniently is prepared by thoroughly mixing a suspension concentrate with a suitable wax. The formulations for spray, dip or drench applications may be prepared upon dilution of a concentrate such as, e.g. an emulsifiable concentrate, a suspension concentrate or a soluble liquid, with an aqueous medium. Such concentrate in most instances consists of the active ingredients, a dispersing or suspending agent (surfactant), a thickening agent, a small amount of organic solvent, a wetting agent, optionally some anti-freeze agent, and water.

The fungicidal compositions of the present invention can also be used for protecting seed against fungi. To that effect the present fungicidal compositions can be coated on seed, in which case the seed grains are drenched consecutively with a liquid composition of the active ingredients or if they are coated with a previously combined composition.

The combination of components (I) and (II) is preferably applied in the form of compositions wherein both said components are intimately admixed in order to ensure simultaneous administration to the materials to be protected. Administration or application of both components (I) and (II) can also be a "sequential-combined" administration or application, i.e. component (I) and component (II) are administered or applied alternatively or sequentially in the same place in such a way that they will necessarily become admixed together at the locus to be treated. This will be achieved namely if sequential administration or application takes place within a short period of time e.g. within less than 24 hours, preferably less than 12 hours. This alternative method can be carried out for instance by using a suitable single package comprising at least one container filled with a formulation comprising the active component (I) and at least one container filled with a formulation comprising an active component (II). Therefore the present invention also encompasses a product containing:

(a) a composition comprising component (I) (i.e. DDAC) and (b) a composition comprising a component (II), selected from imazalil (II-a), boscalid (II-b), fenhexamid (II-c), pyrimethanil (II-d), thiophanate-methyl (II-e), triflumizole (II-f), azoxystrobin (II-g), dimoxystrobin (II-h), picoxystrobin (II-i), and pyraclostrobin (II-j), as a combination for simultaneous or sequential use, wherein said compositions (a) and (b) are in respective proportions such as to provide a synergistic effect against phytophatogenic fungi. Such products may consist of a suitable package comprising separate containers wherein each container comprises component (I) or one of the components (II), preferably in formulated form. Such formulated forms in general have the same composition as described for the formulations containing both active ingredients.

Appropriate carriers and adjuvants for use in the compositions of the present invention may be solid or liquid and correspond to suitable substances known in the art of formulation, such as, for example natural or regenerated mineral substances, solvents, dispersants, surfactants, wetting agents, adhesives, thickeners, binders, fertilizers or anti-freeze agents.

Apart from both the aforementioned components (I) and (II), the compositions according to the present invention may further comprise other active ingredients, e.g. other microbiocides, in particular fungicides, and also insecticides, acaricides, nematicides, herbicides, plant growth regulators and fertilizers.

The components (I) and (II) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, are chosen in accordance with the intended objectives and the prevailing circumstances.

The formulations, i.e. the compositions, preparations or mixtures comprising the active ingredients and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Appropriate carriers and adjuvants for use in the compositions of the present invention may be solid or liquid and correspond to suitable substances known in the art for preparing formulations for treating plants or the loci thereof, or for treating plant products, in particular for treating wood, such as, for example, natural or regenerated mineral substances, solvents, dispersants, surfactants, wetting agents, adhesives, thickeners, binders, fertilizers, anti-freeze agents, repellents, colour additives, corrosion inhibitors, water-repelling agents, siccatives, UV-stabilizers and other active ingredients.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of ligno-sulfonic acid, of dodecylsulfate or of a mixture of fatty alcohol sulfates obtained from natural fatty acids These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutyinaphthalene-sulfonic acid, or of a naphthalene-sulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopoly-propylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxy ethanols, castor oil polyglycol ethers, polypropylene/polyethylene oxide adducts, tributylphenoxy-polyethoxyethanol, polyethylene glycol and octylphenoxy-polyethoxy-ethanol. Fatty acid esters of polyethylene sorbitan, such as polyoxyethylene sorbitan trioleate, are also suitable non-ionic surfactants.

Particularly advantageous additives useful to improve the application and reduce the dose of the active ingredients, are the natural (animal or plant) or synthetic phospholipids of the cephalin or lecithin type such as, for example, phosphatidylethanolamine, phosphatidylserine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylchlorin mixtures. Synthetic phospholipids are for instance, dioctanylphosphatidylchloline and dipalmitoylphosphatidylcholine.

EXPERIMENTAL PART

Experiment 1: Curative Treatment by Dipping

Aqueous test solutions were prepared with concentrations of 10 µg/ml, 100 µg/ml and 1000 µg/ml of DDAC (I); and 500 µg/ml of imazalil (II-a). These test solutions were used to prepare mixtures comprising component (I) and component (II-a) with a concentration respectively of 1000 µg/ml of (I) and 500 µg/ml of (II-a); 100 µg/ml of (I) and 500 µg/ml of (II-a) and 10 µg/ml of (I) and 500 µg/ml of (II-a).

Lemons were artificially inoculated with a 10 mm diameter cork borer dipped in a spore suspension containing $10^6$ cfu/ml of *Penicillium digitatum*. The lemons were treated after 24 hours by submerging for 30 seconds in one of the test solutions.

Treated and untreated lemons were incubated for 14 days in a dark climate room at 20° C. After the incubation period, the diameter of fungal growth was measured and % efficacy (growth inhibition) versus control was calculated. Fungal growth was quantified by measuring the distance, in mm, between the perimeter of the 10 mm diameter inoculation ring and the perimeter of the damaged zone.

Possible synergy was investigated using Limpel's formula (Richter, D. L., *Pestic. Sci.* 1987, 19: 309-315):

$$E_c = X + Y - [(X \cdot Y)/100]$$

where $E_c$ is the expected additive response, or calculated activity, X is the observed percentage control when component A is applied alone and Y is the observed percentage control when component B is applied alone. Synergy was considered to occur when the observed effect, or measured activity, of a combination of both components was greater than the corresponding $E_c$ value.

TABLE 1 efficacy of DDAC (I) and imazalil (II-a) against *Penicillium digitatum* on lemon after 14 days incubation

| Compound | Test concentration (µg/ml) | % Efficacy | % Synergy |
|---|---|---|---|
| DDAC (I) | 1000 | 22 | — |
|  | 100 | 0 | — |
|  | 10 | 0 | — |

TABLE 1-continued efficacy of DDAC (I) and imazalil (II-a) against *Penicillium digitatum* on lemon after 14 days incubation

| Compound | Test concentration (μg/ml) | % Efficacy | % Synergy |
|---|---|---|---|
| Imazalil (IIa) | 500 | 78 | — |
| (I) + (II-a) | 1000 + 500 | 93 | 10 |
|  | 100 + 500 | 84 | 6 |
|  | 10 + 500 | 91 | 13 |
| Water (control) | — | 0 | — |

Experiment 2: Poison Plate Assay

Activity against fungal growth was determined with the poison plate assay. A calculated amount of a stock solution (containing either DDAC, boscalid, fenhexamid, pyrimethanil, thiophanate-methyl, triflumizole, azoxystrobin, dimoxystrobin, picoxystrobin, or pyraclostrobin in a concentration of 500 ppm in dimethyl sulfoxide) was pipetted into 24-well plates in order to reach a final test concentration ranging from 0.21 to 5 ppm in 12 steps when mixed with a culture medium. These culture media were either Glucose Agar (GA) (10 g glucose, 1.5 g $K_2HPO_4$, 2 g $KH_2PO_4$, 1 g $(NH_4)_2SO_4$, 0.5 g $MgSO_4$ and 12.5 g agar in 1 liter deionised water) when pyrimethanil was used as the test substance or Potato Dextrose Agar (PDA) (4 g potato infusion, 20 g bacto dextrose and 15 g bacto agar in 1 liter deionised water) for any of the other test substances. The medium was inoculated with 2 μl of a spore/mycelium suspension. The 24-well plates were kept in the dark at a temperature of 22° C., and a relative humidity of 75% and evaluated for fungal growth after one week.

The following fungi species were used in the poison plate assay: *Penicillium digitatum* strain Sas (sensitive to demethylase inhibiting fungicides), *Penicillium digitatum* strain LDW930223 (reduced sensitivity to demethylase inhibiting fungicides), *Penicillium italicum* strain H17 (reduced sensitivity to demethylase inhibiting fungicides), *Botrytis cinerea* strain BC03019, *Geotrichum candidum*, or *Gloeosporium album* strain A18.

The lowest concentration in ppm of each test compound or mixture of test compounds sufficient to inhibit visible growth was taken as the minimum inhibitory concentration (MIC). When no fungal growth was observed, the abbreviation "ng" was used in Table 2. Synergy was calculated using the Synergy Index method described by von Kull et al. (F. C. Kull, P. C. Eismann, H. D. Sylvestrowicz, R. L. Mayer, 1961, Applied Microbiology 9: 538-541).

Synergistic Index (SI)=(x/m)+(y/n)
- m and n are the MIC values of test substances 1 and 2 respectively, when applied alone
- x and y are the respective quantities of test substances 1 and 2 in mixtures which also cause the complete inhibition of fungal growth, i.e. x and y equal [quantity of test substances 1 and 2, resp., in the mixture (e.g. 0.8 and 0.2, 066 and 0.33 . . . )] multiplied by [MIC-value of the mixture]. If the synergy index equals 1, the combination shows an additive effect. A result smaller than 1 indicates a synergistic effect of the combination.

When the MIC value of a compound was greater than 5 (the highest test concentration) 6.66 was used as MIC value (1 step higher in the dose range) in order to make the calculation of a Synergy Index (SI) possible.

TABLE 2

MIC-values (minimum inhibitory concentration in ppm total a.i.) and synergy index (SI) of DDAC with post harvest fungicides against the fruit pathogen *Botrytis cinerea*

| % DDAC + % test substance | Test substance | | | | | |
|---|---|---|---|---|---|---|
|  | boscalid | | fenhexamid | | pyrimethanil | |
|  | MIC | SI | MIC | SI | MIC | SI |
| 100 + 0 | >5 | na | >5 | na | 5 | na |
| 80 + 20 | 5 | 0.75 | 2.11 | 0.52 | 3.75 | 0.96 |
| 66 + 33 | 5 | 0.75 | 2.11 | 0.66 | 2.11 | 0.61 |
| 50 + 50 | >5 | * | 1.58 | 0.62 | 2.11 | 0.71 |
| 33 + 66 | >5 | * | 1.19 | 0.56 | 2.11 | 0.81 |
| 20 + 80 | >5 | * | 1.19 | 0.64 | 2.11 | 0.88 |
| 0 + 100 | >5 | na | 1.58 | na | 2.11 | na |

| % DDAC + % test substance | Test substance | | | | | |
|---|---|---|---|---|---|---|
|  | thioph. methyl | | triflumizole | | pyraclostrobin | |
|  | MIC | SI | MIC | SI | MIC | SI |
| 100 + 0 | >5 | na | >5 | na | >5 | na |
| 80 + 20 | 5 | 1.07 | >5 | * | 3.75 | 0.56 |
| 66 + 33 | 3.75 | 0.97 | >5 | * | 5 | 0.75 |
| 50 + 50 | 2.81 | 0.88 | >5 | * | >5 | * |
| 33 + 66 | 1.58 | 0.58 | >5 | * | >5 | * |
| 20 + 80 | 2.11 | 0.86 | >5 | * | >5 | * |
| 0 + 100 | 2.11 | na | >5 | na | >5 | na |

*: synergy index could not be calculated because test concentrations were too low and exact MIC could not be determined
na: not applicable

The invention claimed is:

1. A composition comprising a component (I), DDAC, and a post-harvest antifungal component (II) is imazalil (II-a), wherein the ratio by weight of component (I) to component (II) ranges from 1:50 to 2:1 such as to provide a synergistic antifungal effect, and a carrier.

2. A composition according to claim 1 wherein the amount of component (I) is present in a range from 10 to 1.000 mg/l and the amount of component (II) is present in a range from 10 to 1.000 mg/l.

3. A process for preparing a composition as claimed in claim 1, characterized in that the component (I) and one of the components (II) are intimately mixed with the carrier.

4. A product containing
   (a) a composition comprising component (I), DDAC; and
   (b) a composition comprising a component (II), imazalil (II-a), as a combination for simultaneous or sequential use, wherein said compositions (a) and (b) are in a ratio by weight of component (I) to component (II) ranges from 1:50 to 2:1 to provide a synergistic fungicidal effect.

* * * * *